(12) United States Patent
Uchimiya et al.

(10) Patent No.: US 6,812,381 B2
(45) Date of Patent: Nov. 2, 2004

(54) DNA FRAGMENT HAVING PROMOTER FUNCTION

(75) Inventors: Hirofumi Uchimiya, Kanagawa (JP); Satoshi Arai, Saitama (JP); Takaomi Fushimi, Saitama (JP); Michito Tagawa, Saitama (JP); Hiromitsu Fukuzawa, Saitama (JP)

(73) Assignee: Nissan Chemical Industries, Ltd., Tokyo (JP)

(*) Notice: Subject to any disclaimer, the term of this patent is extended or adjusted under 35 U.S.C. 154(b) by 414 days.

(21) Appl. No.: 09/802,937

(22) Filed: Mar. 12, 2001

(65) Prior Publication Data

US 2003/0101474 A1 May 29, 2003

Related U.S. Application Data

(63) Continuation-in-part of application No. PCT/JP99/04847, filed on Sep. 8, 1999.

(51) Int. Cl.$^7$ .............................. A01H 1/00; A01H 5/00; C12N 15/82
(52) U.S. Cl. ....................... 800/287; 800/298; 536/24.1; 435/252.3; 435/320.1; 435/419
(58) Field of Search ........................... 435/252.3, 320.1, 435/419; 536/24.1; 800/287, 298

(56) References Cited

U.S. PATENT DOCUMENTS 5,888,789 A * 3/1999 Rodriguez ................. 435/69.1

FOREIGN PATENT DOCUMENTS

| JP | 3-277291 | 12/1991 |
| JP | 6-261767 | 9/1994 |
| JP | 9-84587 | 3/1998 |

OTHER PUBLICATIONS

Kim et al. A 20 nucleotide upstream element is essential for the noplaine synthase (nos) promoter activity. Plant Molecular Biology, 1994, vol. 24, pp. 105–117.*
Kawai et al., GenBank Accession No. D10334, Oryza sativa mRNA for adenylate kinase-a, Feb. 2, 1999.*
Juan Jose Valdez-Alarcon et al., Gene, "Characterization of a rice sucrose-phosphate synthase-encoding gene", vol. 170, No. 2, issued May 8, 1996, pp. 217–222.
Hirano H. "Oryzasativa Japonica Wxbgene, promoter region and partial cds.", Database GenBank, Accession No. AB008794, Sep. 2, 1998, & Molecular Biology and Evolution, vol. 15, No. 8, issued Aug. 1998, pp. 978–987.
Lidya B. Canchez et al, "Cloning and heterologous expression of Entamoeba histolytica adenylate kinase and uridylate/cyti-dylate kinase", Gene, No. 209, Nos. 1/2, issued Mar. 16, 1998, pp. 219–228.
Shaochuen Song et al, "Cloning and characterization of the gene encoding Halobacterium haolbium adenylate kinase", Gene, vol. 175, Nos. 1/2, issued Oct. 10, 1996, pp. 65–70.
Mohammed Shahjahan et al., "Cloning and characterization of the gene encoding bovine mitochondrial adenylate kinase isozyme 3", Gene, vol. 107, No. 2, issued Nov. 15, 1991, pp. 313–317.
Z. Lee, et al., Molecular Breeding, vol. 3, No. 1, pp. 1–14, "Comparison of Promoter and Selectable Marker Genes for Use in Indica Rice Transformation", 1997.
C–A. Lu, et al., The Journal of Biological Chemistry, vol. 273, No. 17, pp. 10120–10131, "Sugar Response Sequence in the Promoter of a Rice α–Amylase Gene Serves as a Transcriptional Enchancer", Apr. 24, 1998.
M. Kawai, et al., the Plant Journal, vol. 2, No. 6, pp. 845–854, Molecular Characterization of cDNA Encoding for Adenylate Kinase of Rice (*Oryza sativa L.*), Nov. 1992.
M. Brune, et al., Nucleic Acids Research, vol. 13, No. 19, pp. 7139–7151, "Cloning and Sequencing of the Adenylate Kinase Gene (adk) of *Escherichia coli*", Oct. 11, 1985.

* cited by examiner

*Primary Examiner*—David T. Fox
*Assistant Examiner*—Cynthia Collins
(74) *Attorney, Agent, or Firm*—Oblon, Spivak, McClelland, Maier & Neustadt, P.C.

(57) ABSTRACT

DNA derived from a gene encoding rice adenylate kinase which has a promoter function in a plant. A vector containing the DNA having a promoter function. A bacterium containing the vector, a plant cell transformed with the vector, and a plant regenerated from the plant cell and its seed.

The DNA having a promoter function can be ligated with a structural gene such as a reporter gene and integrated into a vector such as an expression vector. When the DNA having a promoter function is ligated to a vector together with a structural gene encoding a protein and transformed into a host cell, the structural gene is expressed. Further, the expression of a desired gene can be regulated by ligating the desired gene under the control of the DNA fragment.

12 Claims, 1 Drawing Sheet

DNA FRAGMENT HAVING PROMOTER FUNCTION

This application is a Continuation-in-part (CIP) of International Application PCT/JP99/04847 filed on Sep. 8, 1999.

TECHNICAL FIELD

The present invention relates a novel DNA derived from a gene encoding rice adenylate kinase which has a promoter function in the plant body or plant cell and expression of a foreign gene and its regulation using the DNA.

BACKGROUND ART

It is generally known that regulation of a structural gene is associated with a region called a promoter which is located upstream of the structural gene. A promoter is a DNA sequence which is located upstream of a structural gene and contains a signal (the TATA box) which directs an RNA polymerase to initiate transcription toward subsequent protein synthesis.

A specific nucleotide sequence called a cis element which is located upstream of the TATA box is supposed to play an important role in regulation of the strength and expression of the promoter.

For example, deletion studies and DNA-fusion studies on the promoter of a drought-inducible gene (rd29A) isolated from *Arabidopsis thaliana* [Koizumi et al., Gene 129:175–182(1993)] revealed that the cis element that regulates the drought-inducible gene rd29A is a 9-bp sequence of TACCGACAT [Yamaguchi-Shiozaki et al., J. Plant Res., 108:127–136(1995)], and that the above-mentioned 9-bp cis element is essential to the drought-inducibility of the promoter.

On the other hand, the 35S promoter from cauliflower mosaic virus [Guilley et al., Cell 30:763–773(1982)] is one of the well-known promoters for plant transformation and regulates expression of foreign genes introduced into dicotyledonous plants and protoplasts [From et al., Proc. Natl. Acad. Sci., 82:5824–5828(1985)]. Analysis in tobacco [Morell et al., Nature 315:200–204(1985)] and petunia [Sander, Nucl. Acid Res. 15:1543–1558(1987)] demonstrated that the 35S promoter is more than 30 times as strong a promoter as the nopaline synthase promoter. Because of its potent promoter activity in dicotyledons, the 35S promoter is often used for efficient expression of plant-viable foreign structural genes introduced into dicotyledons.

However, the 35S promoter only shows relatively weak activity in agriculturally important gramineous monocotyledons [Hauptmann et al., Plant Cell Rep., 6:265–270 (1987)].

In contrast, the promoter of the maize alcohol dehydrogenase (Adh) gene allows a very low level of expression in protoplasts of dicotyledonous *Nicotiana plumbaginifolia* [Ellis et al., EMBO J., 6:11–16(1987)].

Expression of the 35S promoter and the Adh promoter does not seem amenable to tissue-specific or chemical regulation.

Techniques for efficient expression of foreign structural genes and for regulation of their expression are important to create new practically useful varieties of a wide range of plants by gene recombination in the future.

Hence, there is a demand for a promoter that shows promoter activity in monocotyledons as well as in dicotyledons and is easy to regulate tissue- or site-specifically or by harmless chemicals.

On the other hand, it is known that adenylate kinase (AK) is involved in the energy system in animals, microorganisms and plants [Noda et al., The Enzymes., Academic Press, New York:279–305(1973)].

With respect to plants, induction of adenylate kinase by sucrose in rice [Kawai et al., Ikushugakuzasshi, suppl. 1:253(1994)] and localization of the enzyme in vascular bundles [Kawai et al., J. Plant Physiol. 146:239–242(1995); Kawai et al., Plant Molecular Biology 27:943–951(1995)] have been disclosed.

Two cDNA species encoding rice AK (AK-a and AK-b) have been isolated [Kawai et al., The Plant Journal 2(6): 845–854(1992)]. However, the genomic DNA corresponding to them have not been obtained, and the nucleotide sequence of their promoter region remains unknown.

DISCLOSURE OF THE INVENTION

The object of the present invention is to obtain and provide a novel DNA fragment having a promoter function which enables expression of a fused structural gene in a plant body or plant cells and regulation of the expression by a harmless chemical substance or tissue- or site-specifically.

As a result of their extensive research to solve the above-mentioned problems, the present inventors isolated a promoter region of the rice AK-a gene and found that the promoter region functions as a promoter in other plants to express a foreign gene and regulate its expression. The present invention was accomplished on the basis of the discovery.

The present invention provides a promoter of a gene encoding rice adenylate kinase described below, or a DNA fragment having a promoter function which consists of at least part of the nucleotide sequence shown in SEQ ID NO:1 in the Sequence Listing wherein one or more bases may be deleted, added or replaced as long as the fragment having a function to regulate expression of a structural gene viable in a plant, for example, a DNA of 1443 bp shown in SEQ ID NO:2. The present invention also provides a vector containing the DNA fragment having a promoter function, a bacterium containing the vector and a plant transformed with the vector or the bacterium. The present invention still further provides a method for expression of regulating a recombinant DNA which comprises fusing the DNA fragment having a promoter function to another DNA sequence and introducing the resulting recombinant DNA into a plant.

BEST MODE FOR CARRYING OUT THE INVENTION

Figure 1:
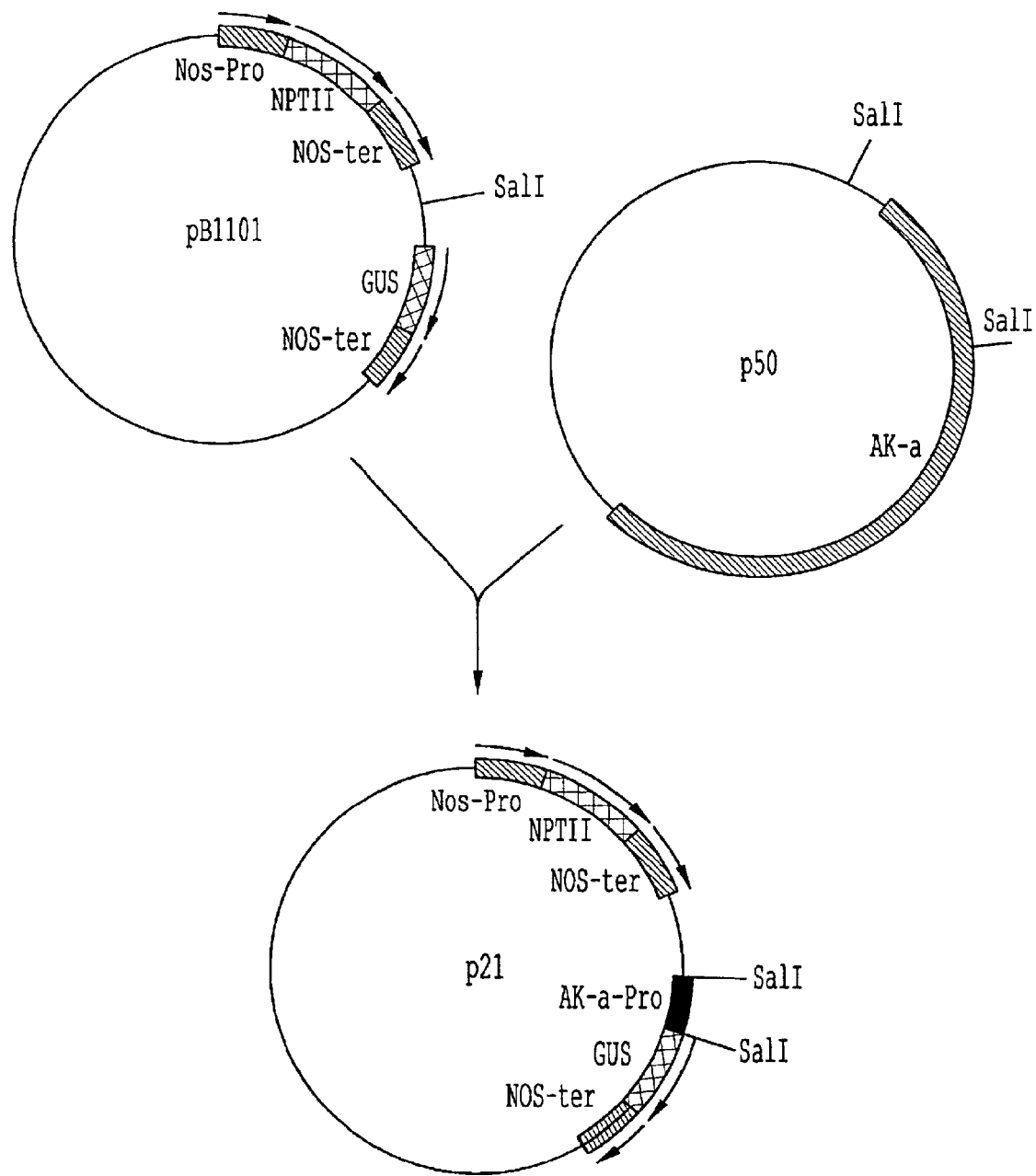
FIG. 1 illustrates the structure of p21. NOS-Pro is the nopaline synthase promoter gene, NPT-II denotes the kanamycin-resistant gene, NOS-Ter denotes the nopaline synthase terminator gene, and AK-a-Pro denotes the AK-a promoter gene.

For the conventional recombinant DNA techniques mentioned hereinafter, reference can be made to Molecular Cloning, Fristch et al., Cold Spring Harbour Press (1989) unless otherwise noted.

The DNA fragment having a promoter function of the present invention can be isolated from a plant genomic library by plaque hybridization using rice AK cDNA as the probe as described below.

The genomic library is obtainable by extracting genomic DNA from a plant such as rice, partially digesting the isolated genomic DNA with an appropriate restriction enzyme such as Sau3A and separating long 9 to 23-bp DNA fragments by sucrose gradient centrifugation or agarose gel electrophoresis, introducing and packaging the DNA fragments in an appropriate vector such as λ phage and incubating *Escherichia coli* such as XL-1 Blue strain infected with the recombinant phage on a culture plate such as an LB plate (1% Bacto tryptone, 0.5% yeast-extract, 1% NaCl, 1.3% agarose). As the vector, λ phage or a cosmid vector is preferable for their ability to accommodate longer inserts though a plasmid is available too.

A membranes such as a nylon membrane is placed on the above-mentioned culture plate, soaked in a denaturing solution, then a neutralizing solution and washed with a washing solution so that the recombinant DNA is adsorbed on the membranes in the form of single strands.

As the probe, a synthetic oligo DNA identical to part of the AK structural gene or part of AK cDNA amplified by PCR using AK cDNA as the template may be used after labeled with [α-$^{32}$P]dCTP, DIG (Digoxigenin), biotin or the like.

The labeled probe is hybridized with the single-stranded DNA on the membrane.

After hybridization with the labeled probe, the clones strongly hybridized with the probe are detected by autoradiography of the membrane and isolated as positive clones.

The DNA from the isolated positive clones is subcloned into an appropriate cloning vector such as pBluescript II after treatment with an appropriate restriction enzyme such as EcoRI, and the nucleotide sequence is determined by the Maxam-Gilbert method or the dideoxy method. Commercial kits are available for the sequencing, and an autosequencer or the like is also available to automate the sequencing.

From the nucleotide sequence of the cloned DNA, the 5' untranslated region of the AK gene and the promoter region which lies upstream of the untranslated region can be identified.

A structural gene such as a reporter gene, an insecticidal protein gene, a herbicide resistant gene, an antibacterial gene, a flowering-inducing gene, a plant growth regulatory gene, a plant morphogenetic gene, a stress resistant gene, a flower pigmenting gene, a phototoxicity resistant gene, a harvest enhancing gene or the like can be ligated downstream of the promoter region.

The reporter gene may be a β-glucuronidase (GUS) gene, a luciferase gene, a chloramphenicol acetyltransferase (CAT) gene or the like. The insecticidal gene may be a crystalline protein gene from *Bacillus thuringiensis*, a protease inhibitor gene or the like. The herbicide resistant gene may be a glyphosate resistant gene, a glufosinate resistant gene, a sulfonylurea herbicide resistant gene or the like. The antibacterial gene may be a chitinase gene, a glucanase gene, a lysozyme gene, a secropine gene or the like. The flowering inducing gene may be a florigene-producing gene or the like. The plant growth regulatory gene may be a polygalacturonase gene or the like. The plant morphogenetic gene may be the rolC gene or the like. The stress resistant gene may be the fatty acid-unsaturating-enzyme gene (FAD3) or the like. The flower pigmenting-associated gene may be a chalcone synthase gene, a phenylalanine ammonia lyase gene or the like. The phototoxicity resistant gene may be a glutamine synthase gene or the like, and the harvest enhancing gene may be a modified seed storage protein gene, a sucrose phosphate synthase gene or the like.

The recombinant DNA having a structural gene such as a reporter gene downstream of the promoter may be introduced into a plant indirectly or directly.

For indirect introduction, use of Agrobacterium may be mentioned.

For direct introduction, the electroporation method, the particle gun method, the PEG method, the microinjection method, the silicon carbide whisker method, etc. are available.

The plant as the host of the gene may be a cereal plant, a vegetable, a fruiter, a feed crop, a fruiter or an ornamental plant. For example, rice, maize, wheat, barley, grass, sugarcane, asparagus, beet, potato, sweet potato, cyclamen, statice, snapdragon, tobacco, arabidpsis, etc. may be mentioned. The plant may be a monocotyledon or a dicotyledon and may be any species.

Insertion of a drug resistant gene such as the kanamycin or hygromycin resistant gene into the transducing vector or simultaneous introduction of a vector having a drug resistant gene into the plant makes it possible to screen plants for transfer of the promoter and the structural gene by using a drug such as kanamycin or hygromycin. Further, it is possible to identify the intended transgenic plant by analysis of the transgene by PCR or southern hybridization or enzymatic or Western analysis of the protein produced by translation of the introduced structural gene in leaf extract.

The transgenic plant may be bred for seed or may be regenerated from tissues such as leaves or roots through cell differentiation.

The amenability of the AK gene to regulation by sucrose makes it possible to regulate expression of the introduced structural gene fused downstream of the promoter region in the transgenic plant by treating the transgenic plant with sucrose as described below.

When the transgenic plant is a complete plant, the inducer may be applied to the foliage by spraying or to soil or a water culture medium for hydroponics. It is possible to allow a piece of a leaf to redifferentiate in a redifferentiation medium supplemented with sucrose.

Seeds of the transgenic plant may be grown in sucrose solution until they develop shoots and roots.

Cells of the transgenic plant, for example, in the form of a callus, may be cultured in a liquid or solid medium containing sucrose or may be directly supplemented with sucrose solution.

Induction of the promoter introduced in the plant by sucrose can be confirmed by quantitative change in the foreign structural gene fused to it and/or its translation product.

For example, when the structural gene is the GUS gene, induction by sucrose can be confirmed by comparing the GUS activities of a sucrose-treated transgenic plant and an untreated transgenic plant obtained by measuring the fluorescence from 4MU produced by hydrolysis of 4MUG by GUS under ultraviolet light (365 nm).

When the crystalline protein gene from *Bacillus thuringiensis* is used as the structural gene, induction by sucrose can be confirmed by comparing the insecticidal activities of a sucrose-treated transgenic plant and an untreated transgenic plant.

Because the AK gene is localized in vascular bundles, it is possible to regulate the site of expression of the fused foreign gene downstream of the promoter region in the transgenic plant carrying it.

Site-specific expression of the foreign structural gene fused with the promoter can be confirmed by locating the structural gene and/or its translation product in the plant.

For example, when the structural gene is the GUS gene, localization of GUS protein in the transgenic plant can be confirmed by histochemical GUS assay.

In other words, localization of GUS protein can be confirmed by microscopic examination of tissues for the blue color of indigotin hydrolytically produced from 5-bromo-4-chloro-3-indolyl-β-D-glucuronic acid by GUS protein.

Application of the above-mentioned procedure to analysis of expression of a reporter gene fused with various mutant promoters having mutations such as deletions or substitution introduced into the promoter region in a plant makes it possible to identify the regions that govern the sucrose-inducibility and vascular bundle-specificity of the expression. Mutations can be introduced to the promoter region, for example, by preparing deletion mutants of the DNA fragment having a promoter function or by cleaving the DNA fragment having a promoter function with an appropriate restriction enzyme and ligating it after partial deletion.

Further, ligation of the regions that govern the sucrose-inducibility and/or tissue- or site-specificity of the expression makes expression of conventional promoters such as the 35S promoter to be controllable.

Now, the present invention will be described in further detail with reference to Examples, but it should be understood that the present invention is by no means restricted thereto.

EXAMPLE 1

Construction of a Rice Genomic Library

The genomic DNA was extracted and isolated from leaves of 2-week-old rice foliage (Nihonbare) for use in construction of a rice genomic library. The isolated genomic DNA was partially digested with Mbo I. The lysate was extracted with phenol-chloroform, and the resulting aqueous layer afforded the Mbo I fragments of the genomic DNA after ethanol precipitation followed by dissolution in TE buffer.

The resulting Mbo I fragments of the genomic DNA were introduced to the Xho I site in a phage vector λ-GEM12 and packaged into phage particles. The recombinant phage was plated on a NZYM (1% NZ amine, 0.5% Yeast Extract, 0.5% NaCl, 0.2% $MgSO_4.7H_2O$ and 1.3% agarose) plate together with top agar containing *Escherichia coli* (KW251) and incubated overnight at 37° C. to form plaques.

EXAMPLE 2

Screening of the Rice Genomic Library (a) Preparation of a Membrane

The NZYM plate having plaques on it was refrigerated, and a membrane (Hybond N+, Amersham) with pencil marks was placed on the plate for 2 minutes and detached after the plate was needled through the membrane for marking. The membrane was denatured in 1.5M NaCl, 0.5M NaOH for 2 minutes, neutralized in 1.5 M Tris-HCl (pH 7.5), 2×SSC for 5 minutes, rinsed in 0.2 M Tris-HCl (pH 7.5), 2×SSC for 30 seconds and dried on a filter paper to immobilize the recombinant DNA from the NZYM plate in the form of single strands.

(b) Preparation of a Probe

A probe was prepared from AK-a cDNA isolated in accordance with Kawai et al., [Kawai et al., The Plant Journal 2(6):845–854(1992)] as follows by using a Random Primer DNA Labeling Kit Ver. 2.0 (TaKaRa) for labeling of the DNA. 1 μg of AK-a cDNA and 2 μl of Random Primer were put in a tube, and sterilized water was added to a total volume of 14 μl. The resulting solution was mixed with 2.5 μl of 10×Buffer, 2.5 μl of dNTP Mixture and 5 μl of [α-$^{32}$P]dCTP (1.85 MBq) and then with 1 μl of Exo-free Klenow Fragment, maintained at 37° C. for 10 minutes and then heated at 65° C. to give a probe.

(c) Hybridization

The above-mentioned membrane carrying single-stranded DNA was put into a hybribag, and a hybridization buffer (5×SSC, 5×Denhard's solution, 0.5% SDS) in an amount of 5 ml per 100 $cm^2$ of the membrane and previously sonicated, heated and quenched salmon sperm DNA at a final concentration of 0.1 mg/ml were added. Then, the above-mentioned labeled probe was added at $10^5$ to $10^6$ cpm per 1 ml of the hybridization buffer after heating and quenching. The bag was sealed and maintained at 65° C. overnight for hybridization. After the hybridization, the membrane was washed in washing solution A (0.1% SDS, 2×SSC) at room temperature for 10 minutes with shaking, then in washing solution B (0.1% SDS, 1×SSC) at 65° C. for 30 minutes with shaking and again in fresh washing solution B at 65° C. for 30 minutes with shaking and then air-dried.

(d) Autoradiography

The air-dried membrane was wrapped with plastic film and subjected to autoradiography to obtain an autoradiogram. The marks on the membrane projected on the autoradiogram were fitted to the marks in the agar plate to spot firmly hybridized phage clones as positive from the positive signals on the autoradiogram, and 11 out of about 2 million phage clones were isolated as positive clones.

EXAMPLE 3

Determination of the Nucleotide Sequence (a) Preparation of Positive Phage DNA

DNA was prepared from the isolated 11 positive phage clones as follows. Each phage clone was suspended in 100 μl of SM buffer (0.58% NaCl, 0.2% $MgSO_4.H_2O$, 0.01% gelatine, 0.05% Tris-HCl) and left to stand at room temperature for 1 hour. 20 μl of *Excherichia coli* (KW251) was added, then maintained at 37° C. for 15 minutes and incubated at 37° C. overnight in 5 ml of NZYM medium. After the incubation, the cultures were shaken with 100 μl of chloroform and centrifuged. To the resulting supernatants containing the phage were incubated together with 5 μg/ml of RNase A and DNase I at 37° C. for 30 minutes, then mixed with the equal volume of 20% PEG6000-2.5 NaCl and left to stand in ice and centrifuged. The resulting pellets were suspended in 500 μl of SM buffer, then maintained at 65° C. for 15 minutes together with EDTA (at a final concentration of 10 mM) and SDS (at a final concentration of 0.1%) and extracted with phenol, phenol-chloroform and chloroform. The resulting aqueous layer was mixed with the equal volume of isopropanol, left to stand at –80° C. for 10 minutes and centrifuged. The resulting pellets were rinsed with 70% ethanol, centrifuged again and dissolved in 50 μl of TE buffer to give phage DNA solution.

(b) Determination of the Nucleotide Sequence of the Positive Phage DNA

The DNA from each phage clone thus obtained was treated with several restriction enzymes including Sac I, Xba I and Pst I and fractionated by agarose gel electrophoresis. After Southern analysis using the entire AK-a cDNA as the probe, the Sac I fragment (1500 bp) from 4-1 and the Xba I fragment (about 2000 bp) from 4-1 were recovered from the agarose gel by using centrifugal filter tubes for DNA recovery (SUPREC-01, TaKaRa) as putative fragments containing regions homologous to AK-a cDNA. The recovered DNA fragments were ligated separately into the restriction sites (Sac I and Xba I) of pBluescript II (STRATAGENE) with DNA Ligation Kit (TaKaRa) and transformed into *Escherichia coli* (XL1-Blue) to obtain two clones: clone p3-2-1 containing the Sac I fragment from 4-1, and clone p-4-2-1 containing the Xba I fragment from 4-1. The nucleotide sequences of both clones were determined by the dideoxy method by using a sequencing kit (Bca BEST Dideoxy Sequencing Kit, TaKaRa). The results indicated not only inclusion of a region homological to AK-a cDNA but also the absence of the desired region upstream from the translation initiation site.

Then, the 11 positive phage clones were screened by Southern analysis using the two DNA fragments obtained by Sac I reaction of the insert in above-mentioned p4-2-1 as the probes after restriction reaction with Sac I followed by agarose gel electrophoresis to identify a positive phage clone (4-1) as putatively containing the upstream region of Ak-a cDNA, which was subjected to Southern analysis using the two DNA fragments obtained by Sac I reaction of the insert in above-mentioned p4-2-1 as the probes after reaction with combinations of Sac I with other twelve restriction enzymes including Sac I-Pst I, Sac I-BamH I and Sac I-Sal I and agarose gel electrophoresis. The Pst I fragment from 4-1, which was presumed to contain the region of AK-a upstream of the translation initiation site from these Southern analyses, was recovered from the agarose gel by using a centrifugal filter tubes for DNA recovery (SUPREC-01, TaKaRa). The recovered DNA fragment was ligated into the restriction site (Pst I) of pbluescript II (STRATAGENE) with DNA Ligation Kit (TaKaRa) and transformed into *Escherichia coli* (XL1-Blue) for subcloning to obtain a clone (p50) containing the Pst I fragment from 4-1. The nucleotide sequences of p50 thus obtained and several deletion mutant clones having deletions of different lengths obtained from p50 by using Deletion Kit for Kilo-Sequence (TaKaRa) were determined by the dideoxy method with a sequencing kit (Sequencing High-Cycle-, TOYOBO), (c) Analysis of the Sequencing Results Analysis of the nucleotide sequences of p3-2-1, p4-2-1 and p50 thus determined with genetic information analysis software (GENETYX-MAC Ver. 8, Software Development Co., Ltd.) revealed the nucleotide sequence of about 4.3 Kb shown in SEQ ID NO:1 emerged. The bases 1340–1580, 2859–3004, 3092–3211, 3332–3499 and 4139–4228 in the nucleotide sequence SEQ ID NO:1 agreed with the previously reported nucleotide sequence of AK cDNA [Kawai et al., The Plant Journal 2(6):845–854(1992)]. Analysis of AK cDNA spotted the translation initiation codon (ATG) at bases 1478–1480 in SEQ ID NO:1 in the Sequence Listing.

Promoter analysis using genetic information analysis software (GENETYX-MAC Ver. 8, Software Development Co., Ltd.) spotted TATA box sequences at bases 946–953 (8 bp) and bases 952–957 (6 bp) in SEQ ID NO:1.

EXAMPLE 4

Assay of Promoter Activity (a) Gene Transfer into a Plant p50 from Example 3 was reacted with Sal I and separated by agarose gel electrophoresis, and the DNA fragment containing 1443 bp (SEQ ID NO:2 in the Sequence Listing) upstream from the translation initiation site (bases 1478–1480 in SEQ ID NO:1) was recovered from the agarose gel by using a centrifugal filter tube for DNA recovery (SUPREC-01, TaKaRa). The DNA fragment was inserted into the Sal I site of a transducing vector for a plant having the kanamycin resistant gene (pBI101, CLONTECH), and the resulting vector shown in FIG. 1 was designated as p21. p21 was introduced into Agrobacterium (LBA4404 strain) as follows.

Agrobacterium was grown in liquid YEP medium (congainin 1% Bacto-peptone, 1% Bacto-yeast extract and 0.5% NaCl) at 28° C. until the absorbance at 600 nm reached about 1.0 and cooled on ice and centrifuged. The cell pellet was suspended in 1 ml of 20 mM CaCl2, frozen in liquid nitrogen, then thawed at 37° C. for 5 minutes together with 1 μg of p21 DNA and incubated in 1 ml of liquid YEP medium at 28° C. for 4 hours with gentle shaking. The culture was centrifuged, and the resulting cell pellet was suspended in 0.1 ml of liquid YEP medium and plated on a YEP plate (containing 1.3% agarose, 25 μg/ml kanamycin, 300 μg/ml streptomycin and 100 μg/ml rifampicin) and incubated at 28° C. for 3 days to obtain transformed Agrobacterium.

The following procedure was followed to achieve gene transfer into tobacco.

The transformed Agrobacterium was grown in liquid YEP medium at 28° C. overnight. Infection was carried out by soaking a 1 cm×1 cm piece of an aseptically grown tobacco leaf in the transformed Agrobacterium culture for 5 minutes. After the infection, the excessive culture medium was removed by sterilized filter paper, and the tobacco leaf was grown on an MS-NB plate under light of about 3000 lux. 5 days later, the leaf was transferred onto an MS-NB plate containing 500 μg/ml claforan to remove the transformed Agrobacterium and cultured. 7 days later, the culture was transferred onto an MS-NB plate (1650 mg/l $NH_4NO_3$, 1900 mg/l $KNO_3$, 440 mg/l $CaCl_2.2H_2O$, 370 mg/l $MgSO_4.7H_2O$, 170 mg/l $KH_2PO_4$, 6.2 mg/l $NH_3BO_3$, 22.3 mg/l $MnSO_4.4H_2O$, 8.6 mg/l $ZnSO_4.7H_2O$, 0.83 mg/l KI, 0.25 mg/l $Na_2MoO_4.2H_2O$, 0.025 mg/l $CuSO_4.5H_2O$, 0.025 mg/l $CoCl_2.6H_2O$, 37.3 mg/l $Na_2$-EDTA, 27.8 mg/l $FeSO_4.7H_2O$, 10 mg/l thiamin hydrochloride, 5 mg/l nicotinic acid, 10 mg/l pyridoxine chloride, 100 mg/l myo-inositol, 2 mg/l glycine, 30000 mg/l sucrose, 0.1 mg/l α-Naphthaleneacetic Acid, 1.0 mg/l 6-Benzyladenine) containing 100 μg/ml kanamycin and 500 μg/ml claforan and grown into a kanamycin resistant culture. When the culture had differentiated into a large kanamycin resistant foliage 10 days later, it was transferred onto a hormone-free MS plate (1650 mg/l $NH_4NO_3$, 1900 mg/l $KNO_3$, 440 mg/l $CaCl_2.2H_2O$, 370 mg/l $MgSO_4.7H_2O$, 170 mg/l $KH_2PO_4$, 6.2 mg/l $NH_3BO_3$, 22.3 mg/l $MnSO_4.4H_2O$, 8.6 mg/l $ZnSO_4.7H_2O$, 0.83 mg/l KI, 0.25 mg/l $Na_2MoO_4.2H_2O$, 0.025 mg/l $CuSO_4.5H_2O$, 0.025 mg/l $CoCl_2.6H_2O$, 37.3 mg/l $Na_2$-EDTA, 27.8 mg/l $FeSO_4.7H_2O$, 10 mg/l thiamin hydrochloride, 5 mg/l nicotinic acid, 10 mg/l pyridoxine chloride, 100 mg/l myo-inositol, 2 mg/l glycine, 30000 mg/l sucrose, 3000 mg/l Gellan gum) and grown to obtain transgenic tobacco.

(b) Confirmation of the Transgene

The presence of the transgene in the transgenic tobacco thus obtained was confirmed by PCR amplification of the genomic DNA extracted by the CTAB method from the transgenic tobacco as the template across the region between the promoter gene and the GUS gene using primers shown in SEQ ID NO:3 and SEQ ID NO:4 followed by agarose electrophoresis. The composition of the reaction solution used in the PCR reaction was as follows. The thermostable DNA polymerase used was TaKaRa EX Taq (TaKaRa).

| | |
|---|---|
| Tris-HCl pH 8.3 | 10 mM |
| KCl | 50 mM |
| $MgCl_2$ | 1.5 mM |
| Each dNPT | 0.2 mM |
| Thermostable DNA polymerase | 1 U |
| Genomic DNA | 0.1 µg |
| Each primer | 20 pmol |

The total volume was adjusted to 50 µl with sterilized water.

The PCR reaction conditions were as follows.

5 minutes at 95° C.

30 cycles of 1 minute at 95° C., 2 minutes at 55° C. and 2 minutes at 72° C.

7 minutes at 72° C.

2% agarose gel electrophoresis of the PCR reaction solution demonstrated the transduction of the AK promoter region and the GUS gene.

(c) Assay of the Promoter Activity

The promoter activity assay was done by measuring the enzymatic activity of the translation product of the reporter gene linked downstream of the promoter (the GUS activity) as follows.

(c-1) Fluorometric Assay

About 100 mg of leaves and roots from the transgenic plant was ground with 100 µl of an extraction buffer (50 mM phosphate buffer (pH 7.0), 10 mM EDTA, 0.1% Triton X-100, 0.1% N-Lauroylsarcosine Sodium Salt, 1 mM β-mercaptoethanol) in a microtube (1.5 ml) on ice and centrifuged to give about 100 µl of a supernatant, which was used for GUS assay and protein assay.

For the GUS assay, 80 µl of the supernatant diluted with 170 µl of the buffer was used as the extracted solution. 250 µl of 4-methyl-umbelliferyl-β-D-glucuronide (4MUG) solution (1 mM 4MUG/extraction buffer) as the substrate was added to the extracted solution, and the reaction was initiated at 37° C. 10 minutes and 40 minutes after the initiation of the reaction, portions (100 µl) of the reaction solution were withdrawn, and 2 ml of a reaction terminative solution (0.2 M sodium carbonate) was added to terminate the reaction. A mixture of 2 ml of the reaction terminative solution and 100 µl of the extracted solution was used as the blank, and mixtures of 2 ml of the reaction terminative solution with 50 µl or 100 µl of 1 µM 4-methyl-umbelliferone (4MU) solution were used as controls. The fluorescence from these solutions was measured with a spectrofluorometer (excitation wavelength=365 nm, emission wavelength=455 nm).

Protein assay was carried out by the Bradford method by using Bio-Rad Protein Assay Kit (BIO-RAD).

The 4MU production per unit time and per unit amount of protein was calculated in pmol/min/mg from the measured values.

| | AK-GUS | Non-transformant |
|---|---|---|
| GUS activity | 98.51 | 14.49 |
| Standard error | 15.61 | 4.37 |

(c-2) Histochemical Assay

A piece of leaf or root tissue was cut from the plant, soaked in a fixing solution (0.3% formamide, 10 mM MES, 0.3 M mannitol) sucked with a vacuum pump and left at room temperature for about 1 hour. The tissue was washed with a buffer (50 mM sodium phosphate pH 7.0), soaked in 5-bromo-4-chloro-3-indolyl-β-D-glucuronic acid (X-Gluc) solution, sucked with a vacuum pump and left at 37° C. for at least 2 hours. The blue color of indigotin was recognized microscopically in the tissue.

EXAMPLE 4

(c-3) Analysis of the Second-Generation Transgenic Plant

Seeds were harvested from the first-generation AK-GUS tobacco showing GUS activity. The seeds were sown and grown into second-generation AK-GUS tobacco. Histochemical examination by staining demonstrated that the AK promoter was functional in the second generation transformant and expressed strongly especially at growing points and vascular bundles.

EXAMPLE 5

Creation of a Herbicide Resistant Plant (a) Gene Transfer into a Plant p50 from Example 3 was reacted with Sal I and separated by agarose gel electrophoresis, and the DNA fragment containing 1443 bp (SEQ ID NO:2 in the Sequence Listing) upstream from the translation initiation site (bases 1478–1480 in SEQ ID NO:1) was recovered from the agarose gel by using a centrifugal filter tube for DNA recovery (SUPREC-01, TaKaRa). The DNA fragment was ligated with a herbicide resistant gene, PPT-acetyltransferase (PAT) gene, and the 35S terminator gene, and inserted into a transducing vector for Agrobacterium to give pNC/AK-PAT. pNC/AK-PAT was introduced into Agrobacterium (LBA4404 and EHA101) by the same method as in Example 3 and transferred into tobacco and rice.

(b) Confirmation of the Transgene

The presence of the transgene in the AK-PAT tobacco and rice thus obtained was confirmed by PCR amplification of the region between the promoter gene and the GUS gene using primers shown in SEQ ID NO:3 and SEQ ID NO:5 followed by agarose electrophoresis in accordance with the CTAB method. Detection of a band of the expected size indicated the presence of the transgene.

(c) Herbicide Resistant Test

The created AK-PAT tobacco and rice were tested for herbicide resistance by application of glufosinate to the foliage. The non-transformants withered to death, while the AK-PAT tobacco and rice were herbicide-resistant and remained viable.

(d) Herbicide Resistant Test of the Second Generation Transductants

Seeds were harvested from the first-generation AK-PAT tobacco and rice expressing herbicide resistance. The seeds could germinate in a glufocinate solution normally. The resulting second-generation AK-PAT tobacco expressed herbicide resistance against glufocinate applied to the foliage.

Industrial Applicability

The promoter of the present invention can induce expression of a useful gene when introduced into a plant or plant cell after ligated with the useful gene. The promoter gene of the present invention is useful as a promoter which makes expression of the introduced useful gene sucrose-inducible because it is the promoter of the sucrose-inducible AK gene. Further, because of localization of AK in vascular bundles, it is possible express the introduced gene in limited tissues or sites.

What is claimed is:

1. An isolated polynucleotide comprising SEQ ID NO: 2.
2. A vector comprising the polynucleotide of claim 1.
3. A host bacterium comprising the polynucleotide of claim 1.
4. A plant cell comprising the polynucleotide of claim 1.
5. A seed comprising the polynucleotide of claim 1.
6. A plant comprising the polynucleotide of claim 1.
7. A plant cell comprising the vector of claim 2.
8. A plant regenerated from the plant cell of claim 4.
9. A seed obtained from a plant which comprises the polynucleotide of claim 1, wherein said seed comprises the polynucleotide of claim 1.

10. A plant cell transformed by a host bacterium comprising the polynucleotide of claim 1, wherein said plant cell comprises the polynucleotide of claim 1.

11. A plant regenerated from a plant cell transformed by a host bacterium comprising the polynucleotide of claim 1, wherein said plant comprises the polynucleotide of claim 1.

12. A seed obtained from a plant regenerated from a plant cell transformed by a host bacterium comprising the polynucleotide of claim 1, wherein said seed comprises the polynucleotide of claim 1.

* * * * *

UNITED STATES PATENT AND TRADEMARK OFFICE
CERTIFICATE OF CORRECTION

PATENT NO. : 6,812,381 B2
DATED : November 2, 2004
INVENTOR(S) : Uchimiya et al.

It is certified that error appears in the above-identified patent and that said Letters Patent is hereby corrected as shown below:

Title page,
Insert Item -- [30]     Foreign Application Priority Data
              Sep. 10, 1998   (WIPO) ..........................PCT/JP98/04088 --

Signed and Sealed this

Eighth Day of February, 2005

JON W. DUDAS
*Director of the United States Patent and Trademark Office*

SEQUENCE LISTING

<160> NUMBER OF SEQ ID NOS: 5

<210> SEQ ID NO 1
<211> LENGTH: 4354
<212> TYPE: DNA
<213> ORGANISM: Oryza sativa L.cv.Nipponbare

<400> SEQUENCE: 1

| | | | | | |
|---|---|---|---|---|---|
| ctgcaggaag | attaattagg | tggacacacc | aaaccctgtg | gttggtgacg | ccctgttgtt | 60 |
| aatcaactgg | ggtgttcgtt | ggacatggtt | tttgcaggaa | aattaagcaa | gaaaattaag | 120 |
| aagaatgctc | aagctgacat | gagaaaacgt | aatccaatgg | aagcgaattt | caagtcgttc | 180 |
| tcttgtacta | ccatgtttag | aatacataag | acagtgccaa | cggtttgatg | gctcctattg | 240 |
| gctcgtgtga | tactgacttg | tgtcacaaag | catcaaattg | cttcttggag | tatctttatt | 300 |
| accgaaaacc | ccaaagatta | ttctattcca | cctcagggta | attgtgctga | actatgcaat | 360 |
| gaatacaaat | tcgcaaaata | tcatggttat | ctatcttgct | caaattgaaa | tttgagtcca | 420 |
| actgagactg | caatacgatt | tttcttttca | aaagaaatt | attaattttt | ttttcatgaa | 480 |
| acgcaattca | accgttcgag | aaatatgctg | tcataaataa | gtagtctagt | gcagaaacaa | 540 |
| aattaatatc | acataaaaaa | gaaggttgtt | aattacaaac | catgtttcgt | actacaactc | 600 |
| taatttgtaa | attcttattt | cagtcacaaa | attccaattt | ccaattaaga | aaaataaacg | 660 |
| tagacggcta | agcccaccca | tctaaggcta | agttcgagag | gtgaagtacg | cacgaaaaat | 720 |
| atgatggttt | attaatatga | ttttttttaa | ataactttca | cataaatttc | tttaggaaac | 780 |
| atatcattta | atggtttgaa | aaacgtgcac | atagaaaact | agaacgatga | gttgggaaac | 840 |
| aagagaaaaa | cacagcctta | aggcttcttg | atcctctagt | tggaggttga | ttttcaaacg | 900 |
| catgataaac | gagaaagctc | attagcacat | tattacttag | atatttataa | ttataaactt | 960 |
| gaaaaaaata | tttatttgaa | ttttttaaac | aatgtatgca | taaattattt | tttaaaaaca | 1020 |
| caccaattta | acccttttaaa | aagcatccta | ataggaaacg | aggaagttaa | agattcaccg | 1080 |
| aaggtgtgtt | tggataatga | aaaatggggt | gggattagaa | ttggtaaatg | aatcagggtt | 1140 |
| aggattaaat | attaaaatga | aagagggaga | atgaatggtt | agagtttaaa | tgtgtctttt | 1200 |
| tggtgggtag | aaaattattt | gccatacact | ccccgagagc | ggtgcgtgct | tgcgtgggca | 1260 |
| gaagcgtctt | tttcgttgga | aaaaaaaact | gcttaaaaag | gaaacagaaa | gagcccagct | 1320 |
| ttggttgtca | ccgtctcacc | agaaacgaaa | caaaaagccc | caccacctaa | acctcctcga | 1380 |
| tccgaccgag | actcctccat | ttcagcggcg | cacgcggaga | gcacgcgacg | cgagttcgtc | 1440 |
| gacgaacaag | gctagtgcag | tagttgttgc | tgcggagatg | gcggcgaacc | tggaggacgt | 1500 |
| gccgtcgatg | gagctgatga | cggagctgct | ccgccgcatg | aagtgcagct | ccaagcccga | 1560 |
| caagcgcgtc | atcctcgtcg | gtaacgcccg | cctctttctt | cttcctctct | ctctctctct | 1620 |
| ctctcggtgg | tttggttcgt | tggttggtgg | atccggttcg | gcggcgcgtg | ctgccctggt | 1680 |
| cgggagatgg | ggaagattg | ctgtggcttg | ctggggatgt | tgcgttagat | ccgtgcaaag | 1740 |
| ctgtctccct | ttctttttttt | gggtcaaatc | tgggtttctt | cttccgctct | cctcgtggtt | 1800 |
| ttttgcaaac | aaaaatgttt | ggcttcgagg | gaatcttgt | aaaatttact | tgttgtttcc | 1860 |
| accttttggaa | actgcggcaa | tttttgatgg | tcaaattgcg | tttgttcttg | caacttgcga | 1920 |
| ttgagtcgat | tggggttttt | ccatttgacg | gaaggatatt | agtgacagaa | atcaagcgaa | 1980 |
| aagaaatatt | tatatgatcg | gtgttcgacg | cataatagga | atttcaggcg | tttaaggtat | 2040 |

-continued

```
agaatttatt cgtattcagt agtatgtgtt gaaattggag gttgcattttt ttgttctcac      2100
acatgttatt ttaaatttgt catgtggcat gtgttgagga tgagcagaaa acaacagggc      2160
ggttcgtggt tttttgtctg atgtggaaac tttttaaaat aaccaaaaca gaaaggtgca      2220
actttatatg tatcgataaa ggtttggaaa tgtcactcgg aataaaaaca aagagataga      2280
cgtattactc ctttgtttca atattcacta gtaaaccaaa tcgatctgta tggttatgta      2340
aactgtgtga cacaacaaat ttcaaataaa cttgttctgt tgcgcaatgc tctgcttcag      2400
caatgcacta ctctaatttta ctggtcatca aacaaatcat tatggaaggt ttattctatt     2460
gttctttttac ttcatgaagt atagctaatt tacaaacact ctgcactacc taatttaagt    2520
ggaccgaatc tagtcatcgt ctgctcttag ctatctccaa attgatggct tgttctaatt      2580
catgcatgtg tcactgagac actggtgttg ttaacagcat tgtaagaatg ccagttacac      2640
cctaatatgt tattgaggat aggatagtgt tgacaacttg atatccatag aggcaaagtg      2700
atgtcaaatt ttgatgcttt tatggatagt ttaataggca tctgggcaga aagcttgaat      2760
attgatgttc tagaatggta agacaatctc tgcgtgttct aaaaaaaaaa aaggtaagac     2820
atacaattttt gacatcccctt tatttttacta aattttaggt ccacctggct gcggaaaggg  2880
aacacagtca ccgctgatta aggatgaatt ttgcttgtgc catttagcca ctggtgatat     2940
gttgagggct gcagtggctg ctaaaactcc acttgggatt aaggctaaag aagctatgga    3000
caaggtagtt tttaagaaac atatagcaac agaaattata accagcagga atgggtttct    3060
tgattctttt gtttctttcc ttatcttcta gggagagctt gtttctgatg acttggttgt    3120
tgggattatt gatgaagcca tgaagaaaac ttcatgccag aaaggttttta tccttgatgg  3180
ttttccctaga actgttgttc aagcacagaa ggtgaggtcc ttggtcaata tgcaccgcta   3240
tataaaagag ctcctttttg ttattagagc tgtctatata aatggacagt ttctatcatt    3300
gtatcacttt tcttactaaa aaatggtgca gcttgatgaa atgttggcca acaaggtac     3360
taagattgac aaggttctaa attttgcaat tgatgatgca atactggaag aacgaattac    3420
cggtcgttgg atccacccat caagtggtag atcttatcat acaaaatttg ctcctcctaa    3480
gactcctgga cttgatgatg taagtcatac cagattactt gctctcgctt gcatttgtca   3540
gatactcaga tttttaccat tttcattatt tctattagat ttggtacata tattgtttga   3600
tgcttgcagc atatgcgcct ttaccataat ttccctgtct catcatcgat catcgtagta   3660
ctctgcttac ttgttttta agaacaaaac atgagccatc attctttcaa aataaaaaag    3720
gttcattgag taccttcttc ttgccactgt ttatttagtt tgcttcccaa atagttaaat    3780
aggtagtgtg attatggata tatttttctt gttttggttg tttctcgtac gaagagtaaa   3840
atgcacctttt tgttgacaag aaatgatagg cagtgtttgc atgacacact tttgcttcct   3900
tttctgacaa ttatgcctgt ttaagtgtcc ataaatagat acatcgacat gttttttgtag  3960
caggagattg tatattgttt ctattgcttc cattaaaagc atattcttct ttagcaatga    4020
tttcatgtgg gacatatttg tgctgctatt aagtaaattt gtttgatatc atatatatct   4080
tttaattggt aatattatgt gcacttctgc tccctgattg ctttgtcttt tcacaaaggt   4140
tactggagaa cccttaattc aaaggaaaga tgacacagct gcagtattga agtcaaggct   4200
tgaagccttc cacgtacaaa ctaagcctgt atgtttcctt tagcaactac gttttttaaat 4260
attcagatat tcttttagga tgtagtcgta cttcagttaa ggcggattcc ttcagttgca   4320
ttacagtgtt tcctgtatat cttttcattgt tttt                               4354
```

<210> SEQ ID NO 2
<211> LENGTH: 1443
<212> TYPE: DNA
<213> ORGANISM: Oryza sativa L.cv.Nipponbare

<400> SEQUENCE: 2

```
ctgcaggaag attaattagg tggacacacc aaaccctgtg gttggtgacg ccctgttgtt      60
aatcaactgg ggtgttcgtt ggacatggtt tttgcaggaa attaagcaa gaaaattaag     120
aagaatgctc aagctgacat gagaaaacgt aatccaatgg aagcgaattt caagtcgttc    180
tcttgtacta ccatgtttag aatacataag acagtgccaa cggtttgatg gctcctattg    240
gctcgtgtga tactgacttg tgtcacaaag catcaaattg cttcttggag tatctttatt    300
accgaaaacc ccaaagatta ttctattcca cctcagggta attgtgctga actatgcaat    360
gaatacaaat tcgcaaaata tcatggttat ctatcttgct caaattgaaa tttgagtcca    420
actgagactg caatacgatt tttcttttca aaagaaatt attaattttt ttttcatgaa     480
acgcaattca accgttcgag aaatatgctg tcataaataa gtagtctagt gcagaaacaa    540
aattaatatc acataaaaaa gaaggttgtt aattacaaac catgtttcgt actacaactc    600
taatttgtaa attcttattt cagtcacaaa attccaattt ccaattaaga aaaataaacg    660
tagacggcta agcccaccca tctaaggcta agttcgagag gtgaagtacg cacgaaaaat    720
atgatggttt attaatatga tttttttttaa ataactttca cataaatttc tttaggaaac    780
atatcattta atggtttgaa aaacgtgcac atagaaaact agaacgatga gttgggaaac    840
aagagaaaaa cacagcctta aggcttcttg atcctctagt tggaggttga ttttcaaacg    900
catgataaac gagaaagctc attagcacat tattacttag atatttataa ttataaactt    960
gaaaaaaata tttatttgaa ttttttaaac aatgtatgca taaattattt tttaaaaaca   1020
caccaatttta acccttttaaa aagcatccta ataggaaacg aggaagttaa agattcaccg  1080
aaggtgtgtt tggataatga aaatggggt gggattagaa ttggtaaatg aatcagggtt    1140
aggattaaat attaaaatga aagagggaga atgaatggtt agagtttaaa tgtgtctttt    1200
tggtgggtag aaaattattt gccatacact ccccgagagc ggtgcgtgct tgcgtgggca   1260
gaagcgtctt tttcgttgga aaaaaaaact gcttaaaaag gaaacagaaa gagcccagct   1320
ttggttgtca ccgtctcacc agaaacgaaa caaaaagccc caccacctaa acctcctcga   1380
tccgaccgag actcctccat ttcagcggcg cacgcggaga gcacgcgacg cgagttcgtc   1440
gac                                                                 1443
```

<210> SEQ ID NO 3
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 3

```
gcccagcttt gttgtcaccg tc                                              22
```

<210> SEQ ID NO 4
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 4

```
cccggctttc ttgtaacgcg ct                                        22

<210> SEQ ID NO 5
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
tgagcgaaac cctataagaa ccc                                       23
```